US007771741B2

(12) United States Patent
Drapeau et al.

(10) Patent No.: US 7,771,741 B2
(45) Date of Patent: Aug. 10, 2010

(54) DEMINERALIZED BONE MATRIX DEVICES

(75) Inventors: Susan J. Drapeau, Cordova, TN (US); Kathy L. Chamness, Memphis, TN (US); William F. McKay, Memphis, TN (US)

(73) Assignee: Warsaw Orthopedic, Inc (US)

( * ) Notice: Subject to any disclaimer, the term of this patent is extended or adjusted under 35 U.S.C. 154(b) by 0 days.

(21) Appl. No.: 11/415,036

(22) Filed: May 1, 2006

(65) Prior Publication Data

US 2007/0254041 A1  Nov. 1, 2007

(51) Int. Cl.
    *A61F 2/28*  (2006.01)
(52) U.S. Cl. .................................. 424/423; 424/488
(58) Field of Classification Search ................. 424/423, 424/488
    See application file for complete search history.

(56) References Cited

U.S. PATENT DOCUMENTS

| | | | |
|---|---|---|---|
| 4,272,948 A | 6/1981 | Dolberg et al. |
| 4,394,370 A | 7/1983 | Jeffries |
| 4,430,760 A | 2/1984 | Smestad |
| 4,440,750 A | 4/1984 | Glowacki et al. |
| 4,472,840 A * | 9/1984 | Jefferies ..................... 128/898 |
| 4,485,097 A | 11/1984 | Bell |
| 4,789,663 A | 12/1988 | Wallace et al. |
| 4,863,732 A | 9/1989 | Nathan et al. |
| 5,124,273 A | 6/1992 | Minami |
| 5,162,114 A | 11/1992 | Kuberasampath et al. |
| 5,273,964 A | 12/1993 | Lemons |
| 5,275,954 A | 1/1994 | Wolfinbarger et al. |
| 5,284,655 A | 2/1994 | Bogdansky et al. |
| 5,290,558 A | 3/1994 | O'Leary et al. |
| 5,298,254 A | 3/1994 | Prewett et al. |
| 5,314,476 A | 5/1994 | Prewett et al. |
| 5,356,629 A | 10/1994 | Sander et al. |
| 5,405,390 A | 4/1995 | O'Leary et al. |
| 5,439,684 A | 8/1995 | Prewett et al. |
| 5,510,396 A | 4/1996 | Prewett et al. |
| 5,513,662 A | 5/1996 | Morse et al. |
| 5,516,532 A | 5/1996 | Atala et al. |
| 5,531,791 A | 7/1996 | Wolfinbarger, Jr. |
| 5,707,962 A | 1/1998 | Chen et al. |
| 5,711,957 A | 1/1998 | Patat et al. |
| 5,811,401 A | 9/1998 | Bucala et al. |
| 5,869,527 A | 2/1999 | Fang et al. |
| 5,948,426 A | 9/1999 | Jeffries |
| 5,972,385 A * | 10/1999 | Liu et al. ..................... 424/486 |
| 6,030,635 A | 2/2000 | Ertzman et al. |
| 6,117,979 A | 9/2000 | Hendriks et al. |
| 6,124,273 A | 9/2000 | Drohan et al. |
| 6,165,487 A | 12/2000 | Ashkar et al. |
| 6,180,606 B1 | 1/2001 | Chen et al. |
| 6,197,325 B1 | 3/2001 | MacPhee et al. |
| 6,200,606 B1 | 3/2001 | Peterson et al. |
| 6,214,368 B1 | 4/2001 | Lee et al. |
| 6,261,586 B1 | 7/2001 | McKay |
| 6,281,195 B1 | 8/2001 | Rueger et al. |
| 6,287,341 B1 | 9/2001 | Lee et al. |
| 6,293,970 B1 | 9/2001 | Wolfinbarger et al. |
| 6,294,041 B1 | 9/2001 | Boyce et al. |
| 6,294,187 B1 | 9/2001 | Boyce et al. |
| 6,297,213 B1 | 10/2001 | Oppermann et al. |
| 6,309,659 B1 | 10/2001 | Clokie |
| 6,311,690 B1 | 11/2001 | Jefferies |
| 6,326,018 B1 | 12/2001 | Gertzman et al. |
| 6,328,765 B1 | 12/2001 | Hardwick et al. |
| 6,331,312 B1 | 12/2001 | Lee et al. |
| 6,340,477 B1 | 1/2002 | Anderson |
| 6,346,515 B1 | 2/2002 | Pitaru et al. |
| 6,368,356 B1 | 4/2002 | Zhong et al. |
| 6,372,257 B1 * | 4/2002 | Marchosky .................. 424/488 |
| 6,437,018 B1 | 8/2002 | Gertzman et al. |
| 6,444,252 B1 | 9/2002 | Gordon et al. |
| 6,444,254 B1 | 9/2002 | Chilkoti et al. |
| 6,458,375 B1 | 10/2002 | Gertzman et al. |
| 6,576,015 B2 | 6/2003 | Geistlich et al. |
| 6,576,016 B1 | 6/2003 | Hochshuler et al. |
| 7,163,691 B2 | 1/2007 | Knaack et al. |
| 2001/0014667 A1 | 8/2001 | Chen et al. |
| 2001/0018614 A1 | 8/2001 | Bianchi |
| 2001/0043940 A1 | 11/2001 | Boyce et al. |
| 2002/0018796 A1 | 2/2002 | Wironen |
| 2002/0034531 A1 | 3/2002 | Clokie |

(Continued)

FOREIGN PATENT DOCUMENTS

RU  2197974 C1  2/2003

(Continued)

OTHER PUBLICATIONS

Progenix DBM Putty and Progenix Plus (2009). Product information from Medtronic. http://manuals.medtronic.com/wcm/groups/mdtcom_sg/@emanuals/@era/@spinal/documents/documents/wcm_prod034012.pdf. downloaded on Feb. 12, 2010. p. 1-2.*

(Continued)

*Primary Examiner*—Taeyoon Kim

(57) ABSTRACT

Described are medical implant devices that include particulate collagen and particulate demineralized bone matrix. These and potentially other materials are held together in a three-dimensionally stable structure such as a porous, resilient sheet, by an ionically-crosslinked polysaccharide gel. Also described are methods for making and using such medical devices.

12 Claims, 1 Drawing Sheet

U.S. PATENT DOCUMENTS

| | | |
|---|---|---|
| 2002/0071827 A1 | 6/2002 | Petersen et al. |
| 2002/0072804 A1 | 6/2002 | Donda |
| 2002/0076429 A1 | 6/2002 | Wironen et al. |
| 2002/0082697 A1 | 6/2002 | Damien |
| 2002/0090725 A1 | 7/2002 | Simpson et al. |
| 2002/0107570 A1 | 8/2002 | Sybert et al. |
| 2002/0151985 A1 | 10/2002 | Kuberasampath et al. |
| 2002/0197242 A1 | 12/2002 | Gertzman et al. |
| 2003/0206937 A1 | 11/2003 | Gertzman et al. |
| 2004/0097612 A1 | 5/2004 | Rosenberg et al. |
| 2005/0020506 A1* | 1/2005 | Drapeau et al. ............... 514/21 |
| 2007/0254041 A1 | 11/2007 | Drapeau et al. |

FOREIGN PATENT DOCUMENTS

| | | |
|---|---|---|
| WO | 9639203 A1 | 12/1996 |
| WO | WO 02/36147 | 5/2002 |
| WO | 200245765 A2 | 6/2002 |
| WO | 03030956 A2 | 12/2002 |
| WO | 03020327 A3 | 3/2003 |
| WO | 2005011764 A1 | 2/2005 |

OTHER PUBLICATIONS

International Search Report PCT/US2004/023557, mailed Mar. 12, 2004.

International Search Report and Written Opinion for PCT/US2008/081544 mailed May 29, 2009.

Eskandari, M.M. et al. (2006). "In vitro re-minerlization of demineralized bone matrix in human serum." Clin Chem Lab Med. 2006;44(1):54-8.

Lee, Kenneth J.H. et al. (2005) "Demineralized bone matrix and spinal arthrodesis" The Spine Journal (5): 217S-223S.

Pacaccio, D. J., et al. (2005). Demineralized bone matrix: basic science and clinical applications. Clin Podiatr Med Surg North Am. Oct. 2005; 22(4): 599-606, vii.

Peitrzak, W.S., et al. (2005) "Demineralized bone matrix graft: a scientific and clinical case study assessment." J Foot Ankle Surg. Sep.-Oct. 2005;44(5):345-53.

Lee, Yo-Po, et al. (2005). "The efficacy of difference commercially available demineralized bone matrix susbtances in an athymic rat model." J Spinal Disord Tech. 2005;18:439-444.

Ranly, Don M., DDS, et al. (2005). "Platelet-derived growth factor inhibits demineralized bone matrix-induced intramuscular cartilage and bone formation." The Journal of Bone of Joint Surgery, Inc., JBJS.org, Sep. 2005; vol. 87-A, No. 9, 2052-64.

Ziran, B., et al. (2005). "Comparative efficacy of 2 different demineralized bone matrix allografts in treating long-bone nonunions in heavy tobacco smokers." Am J Orthop. Jul. 2005;34(7):329-32.

Han, Bo, et al. (2005). "Effect of moisture and temperature on the osteoinductivity of demineralized bone matrix." Journal of Orthopaedic Research, 23 (2005) 855-861.

Colnot, Celine, Ph.D, et al. (2005). "Mechanisms of action of demineralized bone matrix in the repair of cortical bone defects." Clinical Orthopaedics and Related Research, Jun. 2005, No. 435:69-78.

Bender, Sa, et al. (2005). "Evaluation of demineralized bone matrix paste and putty in periodontal intraosseous defects." J Periodontol. May 2005;76(5):768-77.

Schouten, C.C., et al. (2005) "DBM induced ectopic bone formation in the rat: The importance of surface area." Journal of Materials Science: Materials in Medicine, 16 (2005) 149-152.

Peterson, Brett, MD, et al. (2004). "Osteoinductivity of commercially available deminerlized bone matrix." The Journal of Bone and Joint Surgery, Inc., JBJS.org, Oct. 2004; vol. 86-A, No. 10, 2243-50.

Bomback, David A., MD, et al. (2004). "Comparison of posterolateral lumbar fusion rates of grafton putty and OP-1 putty in an athymic rat model." Spine,2004, vol. 29, No. 15, 1612-1617.

Hartman, Ed H.M., MD, et al. (2004). "Demineralized bone matrix-induced ectopic bone formation in rats: In Vivo study with follow-up by Magnetic Resonance Imaging, Magnetic Resonance Angiography, and Dual-Energy X-Ray Absorptiometry." Tissue Engineering, vol. 10, No. 5/6, 2004, 747-754.

Traianedes, Kathy, et al. (2004). "Donor age and gender effects on osteoinductivity of deminerlized bone matrix." J Biomed Mater Res B Appl Biomater. Jul. 15, 2004;70(1):21-9.

Klepp, M, et al. (2004). "Histologic evaluation of demineralized freeze-dried bone allografts in barrier membrane covered periodontal fenestration wounds and ectopic sites in dogs." J Clin Periodontol. Jul. 2004;3 1(7):534-44.

Louis-Ugbo, John, et al. (2004). "Evidence of Osteoinduction by Grafton Demineralized Bone Matrix in Nonhuman Primate Spinal Fusion." Spine, 2004, vol. 29, No. 4, 360-366.

Cammisa, Frank P., Jr., et al. (2004). "Two-Year Fusion Rate Equivalency Between Grafton DBM Gel and Autograft in Posterolateral Spine Fusion." Spine, vol. 29, No. 6, 660-666.

Blum, B, et al. (2004). "Measurement of bone morphogenetic proteins and other growth factors in demineralized bone matrix." Orthopedics. Jan. 2004;27(1Suppl):s161-5.

Etienne, G., et al. (2004). "Use of cancellous bone chips and demineralized bone matrix in the treatment of acetabular osteolysis: preliminary 2-year follow-up." Orthopedics. Jan. 2004;27(1 Suppl):s123-6.

Leatherman, DB, et al. (2004). "The use of demineralized bone matrix for mastoid cavity obliteration." Otol Neurotol. Jan. 2004;25(1):22-5; discussion 25-6.

Yee, Albert Juang Ming MD, et al. (2003). "Augmentation of Rabbit Posterolateral Spondylodesis Using a Novel Demineralized Bone Matrix-Hyaluronan Putty." Spine, vol. 28, No. 21, 2435-2440.

Stavropoulos A., et al. (2003). "Influence of demineralized bone matrix's embryonic origin on bone formation: an experimental study in rats." Clin Implant Dent Relat Res. 2003;5(3):184-92.

Oaks, Daniel A., et al. (2003). "An Evaluation of Human Demineralized Bone Matrices in a Rat Femoral Defect Model." Clinical Orthopaedics and Related Research, No. 413, 281-290.

Han, Bo, et al. (2003). "Quantitative and sensitive in vitro assay for osteoinductive activity of demineralized bone matrix." Journal of Orthopaedic Research, 21 (2003)648-654.

Wilkins, RM, et al. (2003). "The effect of allomatrix injectable putty on the outcome of long bone applications." Orthopedics. May 2003;26(5Suppl):s565-70.

Turner, TM, et al. (2003). "Restoration of large bone defects using a hard-setting, injectable putty containing demineralized bone particles compared to cancellous autograft bone." Orthopedics. May 2003;26(5Suppl):s561-5.

Takikawa, Satoshi, et al. (2003). "Comparative evaluation of the osteoinductivity of two formulations of human demineralized bone matrix." J Biomed Mater Res A. Apr. 1, 2003;65(1):37-42. PMID:12635152 [PubMed—indexed for Medline].

Cook, et al. (2002). "The effect of demineralized bone matrix gel on bone ingrowth and fixation of porous implants." J Arthroplasty. Jun. 2002;17(4):402-8. PMID:12066267 [PubMed—indexed for Medline].

Dickman, Curtis A. (2001). Osteoinductive demineralized bone: what's the risk? Spine. Jul. 1, 2001;26(13):1409-10. No abstract available. PMID: 11458139 [PubMed—indexed for Medline].

Bostrom, MPG, et al. (2001). "An unexpected outcome during testing of commercially available demineralized bone graft materials." Spine, vol. 26, No. 13, 1425-1428.

Wang, Jeffrey C., et al. (2001). "Dose-Dependent toxicity of a commercially available demineralized bone matrix material." Spine, Jul. 1, 2001;26(13):1429-35;discussion 1435-6, PMID: 11458146 [PubMed—indexed for Medline].

Li H, et al. (2000). "Identification of bone morphogenetic proteins 2 and 4 in commercial demineralized freeze-dried bone allograft preparations: pilot study." Clin Implant Dent Relat Res. 2000;2(2):110-7. PMID: 11359264 [PubMed—indexed for Medline].

Maddox, Ewa, et al.,(2000). "Optimizing human demineralized bone matrix for clinical application." Tissue Eng. Aug. 2000:441-8. PMID: 10992439 [PubMed—indexed for Medline].

Russell, James L., (2002). "Grafton Demineralized Bone Matrix: Performance Consistency, Utility, and Value." Tissue Engineering, vol. 6, No. 4, 2000; 435-440.

Russell, JL, et al, (1999). "Clinical utility of demineralized bone matrix for osseous defects, arthrodesis, and reconstruction: impact of processing techniques and study methodology." Orthopedics. May 1999;22(5):524-31; quiz 532-3. Review. PMID: 10348114 [PubMed—indexed for Medline].

Carnes, DL, et al., (1999). "Evaluation of 2 novel approaches for assessing the ability of demineralized freeze-dried bone allograft to induce new bone formation." J Periodontol. Apr. 1999;70(4):353-63. PMID: 10328645 [PubMed—indexed for Medline].

Hagino, T., et al., (1999). "Accelerating bone formation and earlier healing after using demineralized bone matrix for limb lengthening in rabbits." J Orthop Res. Mar. 1999;17(2):232-7. PMID: 10221840 [PubMed—indexed for Medline].

Martin, George J., et al., (1999). "New formulations of demineralized bone matrix as a more effective graft alternative in experimental posterolateral lumbar spine arthrodesis." *Spine*. Apr. 1, 1999;24(7):637-45. PMID:10209791 [PubMed—indexed for Medline].

Garraway R., et al., (1998). "An assessment of the osteoinductive potential of commercial demineralized freeze-dried bone in the murine thigh muscle implantation model." J Periodontol. Dec. 1998;69(12):1325-36. PMID9926762 [PubMed—indexed for Medline].

Edwards, JT., et al., (1998). "Osteoinduction of human demineralized bone:characterization in a rat model." *Clin Orthop Relat Res*. Dec. 1998;(357):219-28. PMID:9917720 [PubMed—indexed for Medline].

Chesmel, KD, et al., (1998). "Healing response to various forms of human deminerlized bone matrix in athymic rat cranial defects." J Oral Maxillofac Surg. Jul. 1998;56(7):857-63; discussion 864-5. PMID: 9663577 [PubMed—indexed for Medline].

Torricelli, P., et al., (1998). "In vitro osteoinduction of demineralized bone." Artif Cells Blood Substit Immobil Biotechnol. May 1998;26(3):309-15. PMID:9635123 [PubMed—indexed for Medline].

Pinholt, EM, et al., (1998). "Osteoinductive potential of demineralized rat bone increases with increasing donor age from birth to adulthood." [PubMed—indexed for Medline] nor age from birth to adulthood. J Craniofac Surg. Mar. 1998;9(2):142-6. PMID:9586543.

Morone, Michael A., et al., (1998). "Experimental Posterolateral Lumbar Spinal Fusion With a Demineralized Bone Matrix Gel." *Spine*. vol. 23(2), Jan. 15, 1998, 159-167.

Zhang, M et al., (1997). "Effect(s) of the demineralization process on the osteoinductivity of demineralized bone matrix." J Peridonontal. Nov. 1997;68(11):1085-92. PMID: 9407401 [PubMed—indexed for Medline].

Caplanis, N. et al., (1997). "Effect of allogeneic, freeze-dried, demineralized bone matrix on guided bone regeneration in supra-alveolar per-implant defects in dogs." Int J Oral Maxillofac Implants. Sep.-Oct. 1997;12(5):634-42. PMID:9337024 [PubMed—indexed for Medline].

Becerra, J., et al. (1996). "Demineralized bone matrix mediates differentiation of bone marrow stromal cells in vitro: effect of age of cell donor." J Bone Miner Res. Nov. 1996;11(11):1703-14. PMID: 8915778 [PubMed—indexed for Medline].

Rabie, AB, et al., (1996). "The effect of demineralized bone matrix on the healing of intramembranous bone grafts in rabbit skull defects." J Dent Res. Apr. 1996;75(4):1045-51. PMID 8708134 [PubMed—indexed for Medline].

Nyssen-Behets C., et al., (1996). "Aging effect on inductive capacity of human demineralized bone matrix." Arch Orthop Trauma Surg. 1996;115(6):303-6. PMID:8905101 [PubMed—indexed for Medline].

Feighan, JE., et al., (1995). "Induction of bone by a demineralized bone matrix gel: a study in a rat femoral defect model." PMID:8544025 [PubMed—indexed for Medline].

Zhang, M. et al., (1997). "A quantitative assessment of osteoinductivity of human demineralized bone matrix." J Peridonontal. Nov. 1997;68(11):1076-84. PMID: 9407400 [PubMed—indexed for Medline].

Toba, Toshinari et al., "Regeneration of Canine Peroneal Nerve with the Use of a Polyglycolic Acid-Collagen Tube Filled with Laminin-Soaked Collagen Sponge: A Comparative Study of Collagen Sponge and Collagen Fibers as Filling Materials for Nerve Conduits," Japan Society for the Promotion of Science, Grant No. JSPS-RFTF 96100203 (2001).

Yarat, A. et al., "A method for preparing collagen graft materials," *J. Marmara Univ. Dent. Fac.*, Sep. 1996;2(2-3):527-9.

CH, Tsai et al., "A composite graft material containing bone particles and collagen in osteoinduction in mouse," *J. Biomed Mater Res.*, 2002;63(1):65-70.

Friess, W. et al., "Effects of processing conditions on the rheological behavior of collagen dispersions," *Eur. J. Pharm. Biopharm*, May 2001; 51(3):259-65.

Doillon, C.J. et al., "Collagen-based wound dressings: control of the pore structure and morphology," J Biomed Mater Res, Oct. 1986, 20(8):1219-28.

Dung, S.Z. et al., "Degradation of insoluble bovine collagen and human dentine collagen pretreated in vitro with lactic acid, pH 4.0 and 5.5," *Arch. Oral Biol.*, Oct. 1994, 39(10):901-5.

Devore, D.P. et al., "Rapidly polymerized collagen gel as a smoothing agent in excimer laser photoablation," *J. Refract. Surg.*, Jan.-Feb., 11(1):50-5, 1995.

Kumar, A.J. et al., "Preoperative embolization of hypervascular head and neck neoplasms using microfibrillar collagen," *AJNR Am. J. Neuroradiol.*, Mar.-Apr. 1982, 3(2):163-8.

Zhang, L. et al., "The modification of scaffold material in building artificial dermis," *Artif. Cells Blood Substit. Immobil. Biotechnol.*, Jul. 2002, 30(4):319-32.

Olde Damink, L.H. et al., "Cross-linking of dermal sheep collagen using a water-soluble carbodiimide," *Biomaterials*, Apr. 1996, 17(8):765-73.

Lee, J.D. et al., "Characterization of UV-irradiated dense/porous collagen membranes: morphology, enzymatic degradation, and mechanical properties," *Yonsei Med. J.*, Apr. 2001, 42(2):172-9.

Pietrucha, K., "Effect of irradiation on collagen solutions in relation to biomedical applications," *Polim. Med.*, 1989, 19(1-2):3-18.

Kuijpers, A.J. et al., "In vivo compatibility and degradation of crosslinked gelatin gels incorporated in knitted Dacron," *J Biomed Mater Res*, Jul. 2000, 51(1):135-45.

Weadock, K.S. et al., "Effect of physical crosslinking methods on collagen-fiber durability in proteolytic solutions," *J Biomed Mater Res*, Oct. 1996, 32(2):221-6.

Roche, S. et al., "Native and DPPA cross-linked collagen sponges seeded with fetal bovine epiphyseal chondrocytes used for cartilage tissue engineering," *Biomaterials*, 2001, 22:9-18.

Schoof, Heike et al., "Control of Pore Structure and Size in Freeze-Dried Collagen Sponges," *J Biomed Mater Res*, 2001, 58:253-357.

Quteish, D. et al., "Development and testing of a human collagen graft material," *J Biomed Mater Res*, Jun. 1990, 24(6):749-60.

Curtil, A. et al., "Freeze drying of cardiac valves in preparation for cellular repopulation," *Cryobiology*, Feb. 1997, 34(1):13-22.

Wissink, M.J. et al., "Endothelial cell seeding on crosslinked collagen: effects of crosslinking on endothelial cell proliferation and functional parameters," *Thromb. Haemost*, Aug. 2000, 84(2):325-31.

Pokharna, H.K. et al., "Collagen crosslinks in human lumbar intervertebral disc aging," *Spine*, Aug. 1998, 23(15):1645-8.

Zeeman, R., et al., "Crosslinking and modification of dermal sheep collagen using 1,4-butanediol diglycidyl ether," *J Biomed Mater Res*, 1999, 46:424-33.

Gratzer, Paul F., et al., "Control of pH Alters the Type of Cross-linking Produced by 1-Ethyl-3-(3-Dimethylaminopropyl)-Carbodiimide (EDC) Treatment of Acellular Matrix Vascular Grafts," *J Biomed Mater Res*, 2001, 58:172-179.

Tachibana, Akira et al., "Fabrication of wool keratin sponge scaffolds for long-term cell cultivation," *Journal of Biotechnology*, 2002, 93:165-170.

Park, Si-Nae et al., "Characterization of porous collagen/hyaluronic acid scaffold modified by 1-theyl-3-(3-dimethylaminopropyl) carbodiimide crosslinking," *Biomaterials*, 2002, 23:1205-1212.

Billiar, Kristen et al., "Effects of carbodiimide crosslinking conditions on the physical properties of laminated intestinal submucosa," *J Biomed Mater Res*, 2001, 56:101-108.

Zeeman, Raymond et al., "The kinetics of 1,4-butanediol diglycidyl ether crosslinking of dermal sheep collagen," *J Biomed Mater Res*, 2000, 51:541-548.

Zeeman, Raymond et al., "Successive epoxy and carbodiimide cross-linking of dermal sheep collagen," *Biomaterials*, 1999, 20:921-931.

Charulatha, V., et al., "Dimethyl 3,3'-dithiobispropionimidate: A novel crosslinking reagent for collagen," *J. of Biomed. Mater Res.*, 2001, 54:122-128.

John, Annie et al., "A trial to prepare biodegradable collagen—hydroxyapatite composites for bone repair," *J Biomater Sci Polymer Edn*, 2001, vol. 12, No. 6, pp. 689-705.

Ueda, Hiroki et al., "Use of collagen sponge incorporating transforming growth factor-β1 to promote bone repair in skull defects in rabbits," *Biomaterials*, 2002, 23:1003-1010.

Sheu, Ming-Thau et al., "Characterization of collagen gel solutions and collagen matrices for cell culture," *Biomaterials*, 2001, 22:1713-1719.

Pieper, J.S. et al., "Development of tailor-made collagen-glycosaminoglycan matrices: EDC/NHS crosslinking, and ultrastructural aspects," *Biomaterials*, 2000, 21:518-593.

Doillon, C.J., et al., "Collagen-based wound dressings: Control of the pore structure and morphology," *J. of Biomed. Mater Res.*, 1986, 20:1219-1228.

Wissink, M.J.B. et al., "Immobilization of heparin to EDC/NHS-crosslinked collagen. Characterization and in vitro evaluation," *Biomaterials*, 2001, 22:151-163.

Wissink, M.J.B. et al., "Binding and release of basic fibroblast growth factor from heparinized collagen matrices," *Biomaterials*, 2001, 22:2291-2299.

Van Wachem, P.B. et al., "In vivo biocompatibility of carbodiimide-crosslinked collagen matrices: Effects of crosslink density, heparin immobilization, and bFGF loading," *J Biomed Mater Res*, 2001, 55:368-378.

Taguchi, Tetsushi et al., "An improved method to prepare hyaluronic acid and type II collagen composite matrices," *J Biomed Mater Res*, 2002, 61:330-336.

Noah, Ernst Magnus et al., "Impact of sterilization on the porous design and cell behavior in collagen sponges prepared for tissue engineering," *Biomaterials*, 2002, 23:2855-2861.

Elbjeirami, Wafa M. et al., "Enhancing mechanical properties of tissue-engineered constructs via lysyl oxidase crosslinking activity," *J Biomed Mater Res*, 2003, 66A:513-521.

Schoof, Heike et al., "Control of Pore Structure and Size in Freeze-Dried Collagen Sponges," *J Biomed Mater Res*, 2001, 58:352-357.

Rocha, Lenaldo B., "Biocompatibility of anionic collagen matrix as scaffold for bone healing", *Biomaterials*, 2002, 23:449-456.

* cited by examiner

DEMINERALIZED BONE MATRIX DEVICES

BACKGROUND

The present invention relates generally to medical implants. In more particular aspects, the present invention relates to osteoinductive medical devices containing demineralized bone matrix.

A wide variety of implant formulations have been suggested in the art for the treatment of bone defects. In addition to traditional bone grafting, a number of synthetic bone graft substitutes have been used or explored, including some materials that contain demineralized bone matrix. Demineralized bone matrix has been shown to exhibit the ability to induce and/or conduct the formation of bone. It is thus desirable to implant and maintain demineralized bone matrix at a site at which bone growth is desired.

However, the beneficial nature of demineralized bone matrix is susceptible to disruption by the incorporation of incompatible materials or techniques when formulating the medical implant material. At the same time, it is desirable to have implant devices exhibiting good physical integrity to retain the demineralized bone matrix at the implant site, and that handle well in the operating environment and during implant. As well, it is of considerable commercial significance that the formulation be manufacturable without undue cost, equipment or material burdens.

In view of the background in the area of demineralized bone matrix devices, there exist needs for product configurations which exhibit the ability to induce and/or support bone growth through the desired region, which are readily manufacturable, and which demonstrate acceptable handling properties for surgeons.

SUMMARY

In one aspect, the present invention provides a sheet-form demineralized bone matrix (DBM) device providing a persistent collagen scaffold in use. The device comprises a resilient, porous sheet including particulate solids, wherein the particulate solids contain a particulate collagen material and a particulate DBM material. Particles of the particulate collagen material are individually chemically or otherwise crosslinked, and the solids are retained in the resilient, porous sheet form by an ionically-crosslinked polysaccharide gel. The DBM material retained in the resilient, porous sheet can exhibit osteoinductivity.

In another aspect, the invention provides a demineralized bone matrix (DBM) device. The device includes a three-dimensionally stable, porous implant structure which comprises particulate solids. The particulate solids include a particulate collagen material and a particulate DBM material in a weight ratio of 1:12 to about 1:2, respectively. The particulate solids are retained in the porous implant structure form by an ionically-crosslinked polysaccharide gel. The DBM material retained in the porous implant structure can exhibit osteoinductivity.

In another aspect, the invention provides a demineralized bone matrix (DBM) device that includes a three-dimensionally stable, porous implant structure. The three-dimensionally stable, porous implant structure comprises particulate solids which include a fragmented bioresorbable sponge material and a particulate DBM material. The fragmented bioresorbable sponge material can comprise a sponge material that has been rendered to particulate form, such as a randomly fragmented (e.g. milled) sponge material. The particulate solids are retained in the porous implant structure form by an ionically-crosslinked polysaccharide gel. The DBM material retained in the porous implant structure can exhibit osteoinductivity.

In another aspect, the invention provides a method for preparing a demineralized bone matrix (DBM) implant material. The method includes preparing an admixture including individually chemically or otherwise crosslinked collagen particles and DBM particles in a liquid medium containing a polysaccharide susceptible to ionic crosslinking. The admixture is contacted with a liquid medium containing a multivalent ionic agent effective to ionically crosslink the polysaccharide so as to form an ionically-crosslinked gel incorporating the DBM and collagen particles. In addition, the method can include the steps of freezing the ionically-crosslinked gel to form a frozen precursor material, and drying the frozen precursor material.

In another aspect, the invention provides a method for preparing a demineralized bone matrix (DBM) implant material. The method includes providing an admixture including collagen particles and DBM particles in a liquid medium containing a polysaccharide susceptible to ionic crosslinking, with the collagen particles and DBM particles present in a weight ratio of about 1:12 to about 1:2. The admixture is contacted with a liquid medium containing a multivalent ionic agent effective to ionically crosslink said polysaccharide, so as to form an ionically-crosslinked gel incorporating the DBM particles and collagen particles. The method can include the further steps of freezing the ionically-crosslinked gel to form a frozen precursor material, and drying the frozen precursor material.

In another aspect, the invention provides a method for preparing a demineralized bone matrix (DBM) implant material. The method includes providing an admixture including a particulated bioresorbable sponge material and osteoinductive DBM particles in a liquid medium containing a polysaccharide susceptible to ionic crosslinking. The admixture is contacted with a liquid medium containing a multivalent ionic species effective to ionically crosslink the polysaccharide, so as to form an ionically-crosslinked gel incorporating the particulated bioresorbable sponge material and DBM particles. The method can include the additional steps of freezing the ionically-crosslinked gel to form a frozen precursor material, and drying the frozen precursor material.

In another aspect, the invention provides a bioactive demineralized bone matrix (DBM) implant device comprising a dried, porous implant body including osteoinductive DBM particles and collagen particles held in intimate contact with one another by an ionically-crosslinked polysaccharide matrix.

In still further aspects, the invention provides methods of treating patients comprising implanting in the patients DBM devices as described herein, and medical products including such devices packaged in sterile condition.

Additional aspects and embodiments, as well as features and advantages thereof, will be apparent to those skilled in the art from the descriptions herein.

DETAILED DESCRIPTION

Figure 1:
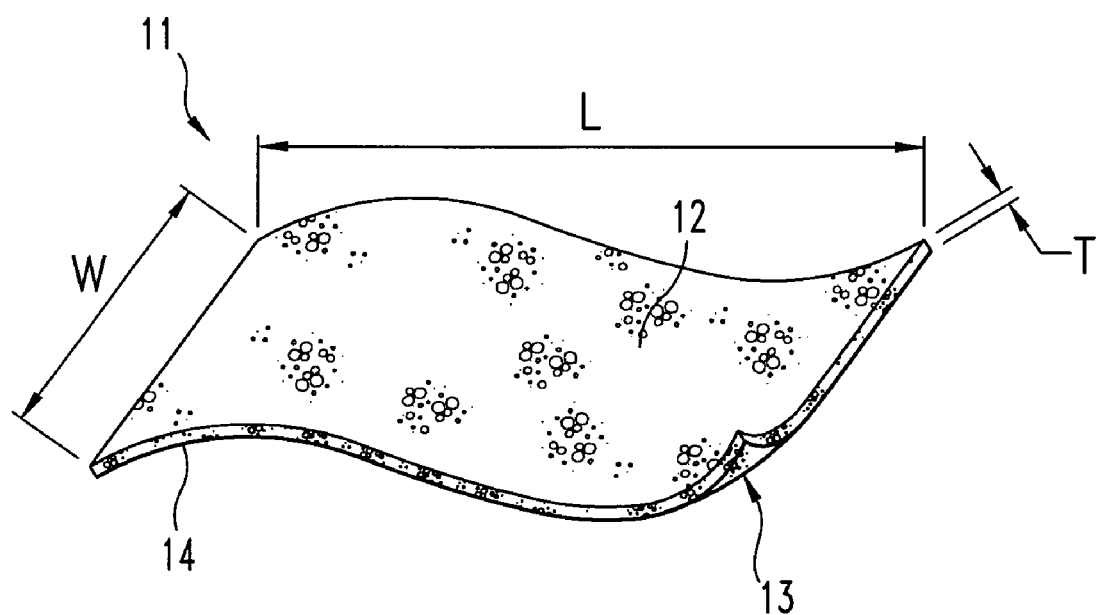
FIG. 1 provides a perspective view of a DBM-containing medical device of the invention.

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

As disclosed above, in certain aspects, the present invention relates to implantable medical devices, and to methods for making and using the devices. In particular embodiments, the present invention provides osteoinductive medical devices that include a three-dimensionally stable structure incorporating particulate solids. The solids include demineralized bone matrix (DBM) particles that in particularly advantageous embodiments are osteoinductive when implanted in a mammalian patient, including a human patient. The solids also include a particulate collagen material, such as collagen fibers or a randomly fragmented bioresorbable material such as a collagen sponge. In certain embodiments, at least some of the collagen particles that are incorporated in the device are individually populated with non-native crosslinks, e.g. by chemical, dehydrothermal, radiation or other crosslinking techniques, to increase their persistence as a scaffold at the implant site after implantation. Devices of the invention advantageously include an ionically-crosslinked polysaccharide matrix which facilitates holding the solids in form. The inventive devices desirably retain the DBM in its bioactive, osteoinductive condition, while also providing beneficial properties during handling and implantation.

The incorporated solids of the disclosed devices include a particulate-form demineralized bone matrix material. In this regard, as used herein, the term "demineralized bone matrix" refers to a matrix material prepared by demineralizing any bone source, including cortical and/or cancellous bone. More desirable demineralized bone matrix materials will contain less than about 5% by weight of residual calcium. The source bone can be from any suitable source including autogenic, allogeneic, and/or xenogenic bone. When used in describing a demineralized bone matrix (DBM) material, the term "osteoinductive" refers to the ability of the DBM material to induce bone growth. Alternatively, DBM materials can be provided lacking osteoinductive character, and nonetheless be used as osteoconductive materials that provide a scaffold capable of receiving bone growth induced by natural healing processes or other materials implanted in the patient.

DBM materials for use in the present invention can be obtained commercially or can be prepared by known techniques. In general, advantageous, osteoinductive DBM materials can be prepared by decalcification of cortical and/or cancellous bone, often by acid extraction. This process can be conducted so as to leave collagen, noncollagenous proteins, and growth factors together in a solid matrix. Methods for preparing such bioactive demineralized bone matrix are well known, in respect of which reference can be made to U.S. Pat. Nos. 5,073,373; 5,484,601; and 5,284,655, as examples. DBM products are also available commercially, including for instance, from sources such as Regeneration Technologies, Inc. (Alachua, Fla.), The American Red Cross (Arlington, Va.), and others. In certain embodiments, the particulate DBM material can have an average particle size of less than about 1,000 μm. For instance, the DBM material can have particle sizes in the range of 50 to 850 μm. DBM materials that are solely osteoconductive can be prepared using similar techniques that have been modified or supplemented to remove or inactivate (e.g. by crosslinking or otherwise denaturing) components in the bone matrix responsible for osteoinductivity. Osteoinductive and/or osteoconductive DBM materials used in the present invention can desirably be derived from human donor tissue, especially in regard to implant devices intended for use in human subjects.

Collagen material that is insoluble in water can be used, and can be derived from natural tissue sources (e.g. xenogenic, allogenic, or autogenic relative to the recipient human or other patient) or recombinantly prepared. Collagens can be subclassified into several different types depending upon their amino acid sequence, carbohydrate content and the presence or absence of disulfide crosslinks. Types I and III collagen are two of the most common subtypes of collagen. Type I collagen is present in skin, tendon and bone, whereas Type III collagen is found primarily in skin. The collagen used in compositions of the invention can be obtained from skin, bone, tendon, or cartilage and purified by methods well known in the art and industry. Alternatively, the collagen can be purchased from commercial sources. Type I bovine collagen is preferred for use in the invention.

The collagen can be atelopeptide collagen and/or telopeptide collagen. Still further, either or both of non-fibrillar and fibrillar collagen can be used. Non-fibrillar collagen is collagen that has been solubilized and has not been reconstituted into its native fibrillar form.

Suitable collagen products are available commercially, including for example from Kensey Nash Corporation (Exton, Pa.), which manufactures a fibrous collagen known as semed F, from bovine hides. Collagen materials derived from bovine hide are also manufactured by Integra Life Science Holding Corporation (Plainsboro, N.J.). Naturally-derived or recombinant human collagen materials are also suitable for use in the invention. Ilustratively, recombinant human collagen products are available from Fibrogen, Inc. (San Francisco, Calif.).

The solid particulate collagen incorporated into the inventive compositions can be in the form of intact or reconstituted fibers, or randomly-shaped particles, for example. In certain beneficial embodiments, the solid particulate collagen will be in the form of particles derived from a sponge material, for example by randomly fragmenting the sponge material by milling, shredding or other similar operations. Such particulated sponge material can have an average maximum particle diameter of less than about 6 mm, more preferably less than about 3 mm, and advantageously in the range of about 0.5 mm to 2 mm. Such materials can, for example, be obtained by milling or grinding a porous sponge material and sieving the milled or ground material through screen having openings that are sized about 6 mm or smaller, desirably sized from about 0.5 mm to about 2 mm. Retch grinders with associated sieves are suitable for these purposes. The resulting small sponge particles are randomly formed and have generally irregular shapes with remnant structures from the sponge material, and are highly beneficial for use in devices of the invention. In this regard, the use of such particulated sponge materials in combination with DBM materials in devices is considered as an inventive aspect disclosed herein also wherein the sponge material is made completely or in part from a bioresorbable material other than collagen. For example, the particulated sponge material can be made from any of the other natural or synthetic polymers disclosed herein. Likewise, in these particulated sponge device embodiments, another binder material or technique can be used instead of the ionically-crosslinked polysaccharide matrix, including for example other gel-forming substances which can, for example, be thermally reversible gel forming agents such as gelatin. As well, the particulated sponge material can optionally be used in the same relative amounts disclosed herein for the collagen solids materials. Further, where a sponge starting material has been chemically crosslinked with an aldehyde crosslinker such as formaldehyde or glutaraldehyde, or another suitable chemical crosslinker such as a carbodiimide, or by other techniques such as dehydrothermal or radiation-induced crosslinking, the particulated collagen or other bioresorbable material retains the chemical crosslinking and provides an advantageous, lasting scaffold for bone ingrowth. Other sources of chemically or otherwise non-naturally crosslinked particulate collagen, in fiber, irregular or other shapes, can also be used to significant advantage in providing lasting organic scaffolds for tissue ingrowth, and their use is considered to be another aspect of the present invention. These crosslinked particulate materials can be provided as starting materials for preparing devices as disclosed herein, and therefore as incorporated in the device these particles are individually crosslinked. Thus, as used herein, the term "individually crosslinked" means that the particles include non-native crosslinks other than those which might be introduced by any crosslinking technique used to hold the solids of the device together as a unitary structure, e.g. by introducing crosslinks between respective particles after they have been cast or otherwise formed into the shape of the device. As well, crosslinked solid collagen particles can be used in combination with non-crosslinked collagen in compositions of the invention, wherein the non-crosslinked collagen can be solid (insoluble) or soluble collagen, or combinations thereof. Such crosslinked and non-crosslinked collagen mixtures can be used, for example, to modulate the residence time of the collagen portion of the implant compositions in vivo.

As noted above, devices of the invention include an amount of collagen. The collagen will desirably be incorporated in a substantial, scaffold-providing amount, but an amount less than that of the particulate DBM on a weight-to-weight basis. In certain compositional embodiments of the invention, the bioresorbable solids include the particulate solid collagen material and the DBM material at a collagen material:DBM material weight ratio (dry basis) of about 1:12 to about 1:2. More desirably, said weight ratio is in the range of about 1:12 to about 1:5, or about 1:10 to about 1:5. Particular inventive embodiments are provided wherein said weight ratio is in the range of about 1:8 to about 1:5. The inventive devices thus include significant amounts of the collagen solids, which provide a local scaffold material for cellular infiltration and eventual new bone volume. Typically, the particles of such collagen solids are less dense than the DBM particles, which not only can improve the physical handling and implant properties of the inventive materials but also provide a local scaffold environment that is more susceptible to cellular infiltration than the DBM particles alone. These factors, combined with the biologically-friendly nature of the ionically-crosslinked polysaccharide matrix contributing to the integrity to the device, provide osteoinductive materials of particular benefit to health care providers and patients.

In regard to the incorporated materials considered on a dry weight basis, the particulate DBM material can constitute about 20% to about 90% of the inventive devices, more preferably about 50% to about 90%, and most preferably about 70% to about 85% by weight. Similarly, on a dry weight basis, preferred devices can contain about 5% to about 30% by weight of the particulate collagen, more preferably about 8% to about 20%, and most preferably about 10% to about 15%.

Considered together, the particulate collagen and DBM materials can at least largely make up the weight of the device on a dry weight basis, for example with these two materials can constitute at least about 50%, at least about 70%, or at least about 80% by weight of the overall device on a dry weight basis. In certain embodiments, the water-insoluble solids in the composition can consist or consist essentially of the collagen particles and DBM particles. As well, in desirable embodiments of the invention, all of the water-insoluble solids in the composition will be bioresorbable. It will be understood, however, that these parameters are not necessary to all aspects of the invention.

In certain aspects of the invention, medical devices are provided which comprise one or more polysaccharides used to form an ionically-crosslinked gel or matrix which participates in providing three-dimensional stability to the devices. Preferred are ionic polysaccharides that are capable of forming thermally irreversible ionically-crosslinked gels upon combination with divalent or other polyvalent cationic materials. Suitable such polysaccharides include, as examples, plant-derived polysaccharides such as alginates and pectins, and gel-forming derivatives thereof. Aqueous solutions of such ionic polysaccharides form ionically-crosslinked gels upon contact with aqueous solutions of counter-ions. For instance, useful agents for ionically crosslinking alginate and pectin polysaccharides include cationic gelling agents, preferably including divalent or trivalent cations. Useful divalent cations for these purposes include the alkaline earth metals, especially calcium and strontium. Aluminum is a useful crosslinking trivalent cation. These ionic crosslinking agents will usually be provided by salts. Useful anionic counter-ions for the calcium or other salts are desirably selected from pharmaceutically-acceptable anions such as chlorides, gluconates, fluorides, citrates, phosphates, tartrates, sulphates, acetates, borates, and the like. An especially preferred ionic crosslinking agent for use with an alginate or pectin compound is provided by calcium chloride. The ionic polysaccharide chitosan can also be used, and can be ionically crosslinked with multivalent, anionic gelling agents. Such agents include metal polyphosphates, such as an alkali metal or ammonium polyphosphate, pyrophosphates or metaphosphates. Citrates can also be used. These anionic crosslinking agents will also usually be provided by salts. The cationic counter-ion for the polyphosphate or other salt can be any suitable, biocompatible or pharmaceutically-acceptable cation including for instance sodium, potassium, or ammonium. Many other biocompatible polysaccharides, including plant-derived and animal-derived materials, as well as corresponding ionic crosslinking agents, are known and can also be used in aspects of the present invention.

The polysaccharide will typically be incorporated into devices of the invention at a relatively low level. Accordingly, in certain inventive variants, when considered on a dry weight basis, preferred inventive devices can contain the polysaccharide at a level of about 1% to about 20%, more preferably about 5% to about 15%, and most preferably about 8% to about 12%. It will be understood, however, that other amounts of polysaccharide can be used within the broader aspects of the present invention. The polysaccharide material, when ionically crosslinked, holds the incorporated particulate solids together and contributes by providing integrity to the overall three-dimensional structure of the device. In this regard, in certain advantageous embodiments, the particulate solids can be bound together to form the device without the use of any chemical crosslinker, such as glutaraldehyde, formaldehyde or a carbodiimide, to covalently link the solid particles to one another. In such devices, the solid particulates are thus held together in the substantial or complete absence of covalent chemical crosslinks between the particles. In other embodiments, covalent chemical crosslinks can be introduced by such chemical crosslinking agents; however, where osteoinductive DBM material is used and preservation of its osteoinductive character is desired, such chemical crosslinking is desirably used at a low, controlled level that does not abrogate such osteoinductive character.

Devices of the present invention can be manufactured in a ready-to-use condition and packaged in medically acceptable packaging in sterile condition, in either wet or dry formats. In some embodiments, as illustrated in FIG. 1, the ready-to-use medical product can be a porous, sheet-form product 11, such as a resilient sponge material. Sheet-form material configured as strips or other parallelepiped three dimensional bodies are readily manufactured, and provide beneficial products. Sheet-form product 11 includes a first face 12, a second face 13, and sidewalls 14 interconnecting the first and second faces 12 and 13. Sheet-form product can have any suitable length (L), width (W) and thickness (T). In certain embodiments, the length and width L and W will range from about 1 cm to about 50 cm, and the thickness T will range from about 0.1 cm to about 10 cm. More typically, the length and width L and W will each range from about 1 cm to about 20 cm, and the thickness T from about 0.2 cm to about 1 cm. From the standpoint of volume, preferred devices will have a body defining a volume of about 0.1 cm$^3$ to 500 cm$^3$, more typically in the range of about 1 cm$^3$ to about 100 cm$^3$, and most typically in the range of about 1 cm$^3$ to about 20 cm$^3$. It will be understood however that other linear and volumetric dimensions can also be employed within the scope of the present invention.

The bulk densities of the inventive devices can vary and depend upon factors such as the extent of their porosity, the densities of the incorporated materials, and the state of the device (e.g. hydrated or dehydrated condition). In certain embodiments, the device will be in a dried condition (containing less than 5% by weight of water or other liquid), and will have a bulk density in the range of about 0.1 g/cc to about 0.4 g/cc, more typically in the range of about 0.1 g/cc to about 0.3 g/cc, and in certain embodiments about 0.15 g/cc to about 0.25 g/cc. Nonetheless, as noted above these densities may vary with many factors, and bulk densities within these ranges, or that are lower or higher, may be exhibited by devices within aspects of the invention.

Devices of the invention can be substantially porous. Desirable devices will have a void volume of at least about 40% and typically in the range of about 40% to 90%, especially when in a dried condition. Moderate void volume levels of about 50% to less than 70%, or higher levels in the range of 70% to 90% or more, can be controllably achieved, for instance by varying the amount of water or other liquid included in a slurry used to prepare the devices and/or varying the lyophilization conditions.

Devices of the invention can be manufactured by preparing a mixture including the DBM material, the polysaccharide, and the collagen material (or the particulated bioresorbable sponge material, be it collagenous or otherwise), along with any other liquid or solid materials to be incorporated in to the device upon original manufacture. This mixture can then be contacted with a liquid medium (e.g. solution) containing the ionic crosslinking agent so as to form the wetted ionically-crosslinked gel material. This wet gel material can be sterilized and packaged in a wetted state; or, the wet gel material can be dried. Such drying advantageously utilizes lyophilization or other sublimation drying techniques that involve freezing the wet gel material and drying the material while frozen. In certain embodiments, the non-crosslinked admixture of materials is charged to a liquid-penetrable mold, such as a porous mold, in a desired shape. The filled mold is then immersed in a solution of the ionic crosslinking agent to form the ionically-crosslinked gel in the shape of the mold. The resultant wetted crosslinked gel can then be packaged and sterilized as the final product, or can be dried and potentially additionally processed as described herein to provide the final product.

The inventive devices can be implanted in the patient in a dried or wetted condition. When wetted, any medically acceptable wetting agent can be used. These include, for example, aqueous substances such as sterile water, physiological saline, phosphate buffered saline, blood, bone marrow, bone marrow fractions or other liquid mediums, emulsions or suspensions that provide adequate wetting characteristics. Biocompatible organic liquids can also be used, alone or in combination with water. A wide variety of biocompatible organic liquids are known and suitable for these purposes, including for instance liquid polyols such as glycerol. In desired forms, molecules of the wetting agent (e.g. water) will be taken up into the dried, ionically-crosslinked polysaccharide matrix to form a wetted, firm gel device incorporating the particulate DBM material, the particulate collagen material, and any other material of the device, e.g. one or more of those additional substances described herein.

Implant devices of the invention may also contain other beneficial substances including for example preservatives, cosolvents, suspending agents, buffering agents (e.g. carrying active agents to be added to the device) viscosity enhancing agents, ionic strength and osmolality adjusters and/or other excipients.

The implant devices disclosed herein can also include other biocompatible and preferably bioresorbable substances. These materials may include, for example, natural polymers such as proteins and polypeptides, glycosaminoglycans, proteoglycans, elastin, hyaluronic acid, dermatan sulfate, or mixtures or composites thereof. Synthetic polymers may also be incorporated into the malleable implant materials. These include, for example biodegradable synthetic polymers such as polylactic acid, polyglycolide, polylactic polyglycolic acid copolymers ("PLGA"), polycaprolactone ("PCL"), poly(dioxanone), poly(trimethylene carbonate) copolymers, polyglyconate, poly(propylene fumarate), poly(ethylene terephthalate), poly(butylene terephthalate), polyethyleneglycol, polycaprolactone copolymers, polyhydroxybutyrate, polyhydroxyvalerate, tyrosine-derived polycarbonates and any random or (multi-)block copolymers, such as bipolymer, terpolymer, quaterpolymer, etc., that can be polymerized from the monomers related to previously-listed homo- and copolymers.

The devices of the invention can also include a mineral component. The mineral used can include a natural or synthetic mineral that is effective to provide a scaffold for bone ingrowth. Illustratively, the mineral matrix may be selected from one or more materials from the group consisting of bone particles, Bioglass®, tricalcium phosphate, biphasic calcium phosphate, hydroxyapatite, corraline hydroxyapatite, and biocompatible ceramics. Biphasic calcium phosphate is a particularly desirable synthetic ceramic for use in the invention. Such biphasic calcium phosphate can have a tricalcium phosphate:hydroxyapatite weight ratio of about 50:50 to about 95:5, more preferably about 70:30 to about 95:5, even more preferably about 80:20 to about 90:10, and most preferably about 85:15. The mineral material can be a granular particulate having an average particle diameter between about 0.2 and 5.0 mm, more typically between about 0.4 and 3.0 mm, and desirably between about 0.4 and 2.0 mm.

In another aspect of the invention, the mineral material can include bone particles, possibly cancellous but preferably cortical, ground to provide an average particle diameter among those discussed above for the particulate mineral material. Both human and non-human sources of bone are suitable for use in the instant invention, and the bone may be autographic, allographic or xenographic in nature relative to the mammal to receive the implant. Appropriate pre-treatments known in the art may be used to minimize the risks of disease transmission and/or immunogenic reaction when using bone particles as or in the mineral material.

In one embodiment, xenogenic bone that has been pre-treated to reduce or remove its immunogenicity is used to provide a porous mineral matrix in the implant device. For example, the bone can be calcined or deproteinized to reduce the risks of immunogenic reactions to the implant material.

Bioactive agents can be delivered with devices of the invention. These bioactive agents may include, for example, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholnergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenlcs, non-steroidal anti-inflammatory agents, steroidal anti-inflammatory agents, antioxidants, vaso-active agents, bone-active agents, osteogenic factors, antiarthritics, and diagnostic agents.

Bioactive agents may also be provided by tissue materials incorporated into the devices, including for instance autologous or allogenic tissue materials, which are incorporated into the material to be implanted in the patient. Such tissue materials can include blood or blood fractions, bone marrow or bone marrow fractions, and/or other sources of cells or other beneficial tissue components derived from the patient to be treated or another suitable animal source. These substances can, for example, be added to the device just prior to implantation into the patient.

Bioactive agents such as those described herein can be incorporated homogeneously or regionally into the implant devices by simple admixture or otherwise. Further, they may be incorporated alone or in conjunction with another carrier form or medium such as microspheres or another microparticulate formulation. Suitable techniques for forming microparticles are well known in the art, and can be used to entrain or encapsulate bioactive agents, whereafter the microparticles can be incorporated within or upon the inventive device during or after its preparation.

In certain embodiments, a device of the invention will include one or more substances, additional to the osteoinductive DBM material, that induces or generates the formation of bone. Suitable osteogenic materials can include a growth factor that is effective in inducing formation of bone. Desirably, the growth factor will be from a class of proteins known generally as bone morphogenic proteins (BMPs), and can in certain embodiments be recombinant human (rh) BMPs. These BMP proteins, which are known to have osteogenic, chondrogenic and other growth and differentiation activities, include rhBMP-2, rhBMP-3, rhBMP4 (also referred to as rhBMP-2B), rhBMP-5, rhBMP-6, rhBMP-7 (rhOP-1), rhBMP-8, rhBMP-9, rhBMP-12, rhBMP-13, rhBMP-15, rhBMP-16, rhBMP-17, rhBMP-18, rhGDF-1, rhGDF-3, rhGDF-5, rhGDF-6, rhGDF-7, rhGDF-8, rhGDF-9, rhGDF-10, rhGDF-11, rhGDF-12, rhGDF-14. For example, BMP-2, BMP-3, BMP-4, BMP-5, BMP-6 and BMP-7, disclosed in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in U.S. Pat. No. 5,637,480; BMP-11, disclosed in U.S. Pat. No. 5,639,638, or BMP-12 or BMP-13, disclosed in U.S. Pat. No. 5,658,882, BMP-15, disclosed U.S. Pat. No. 5,635,372 and BMP-16, disclosed in U.S. Pat. Nos. 5,965,403 and 6,331,612. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of these Patents and applications are hereby incorporated herein by reference. Also useful in the present invention are heterodimers of the above and modified proteins or partial deletion products thereof. These proteins can be used individually or in mixtures of two or more. rhBMP2 is preferred.

The BMP may be recombinantly produced, or purified from a protein composition. The BMP may be homodimeric, or may be heterodimeric with other BMPs (e.g., a heterodimer composed of one monomer each of BMP-2 and BMP-6) or with other members of the TGF-beta superfamily, such as activins, inhibins and TGF-beta 1 (e.g., a heterodimer composed of one monomer each of a BMP and a related member of the TGF-beta superfamily). Examples of such heterodimeric proteins are described for example in Published PCT Patent Application WO 93/09229, the specification of which is hereby incorporated herein by reference. The amount of osteogenic protein useful herein is that amount effective to stimulate increased osteogenic activity of infiltrating progenitor cells, and will depend upon several factors including the size and nature of the defect being treated, and the device and particular protein being employed.

Other therapeutic growth factors or substances may also be used in devices of the present invention, especially those that may be used to stimulate bone formation. Such proteins are known and include, for example, platelet-derived growth factors, insulin-like growth factors, cartilage-derived morphogenic proteins, growth differentiation factors such as growth differentiation factor 5 (GDF-5), and transforming growth factors, including TGF-α and TGF-β.

The osteogenic proteins or other biologically active agents, when used in the present invention, can be provided in liquid formulations, for example buffered aqueous formulations. In certain embodiments, such liquid formulations can be received upon and/or within, or otherwise combined with a dry-form device by a health care provider just prior to implantation. In other embodiments, such liquid formulations can be included within wet materials used to prepare a dry-form or wetted device during its manufacture. One suitable rhBMP-2 formulation is available from Medtronic Sofamor Danek, Memphis, Tenn., with its INFUSE® Bone Graft product.

Osteoinductive devices of the present invention can also comprise progenitor and/or stem cells derived from embryonic or adult tissue sources and/or taken from culture. Illustratively, compositions of the invention can incorporate cells derived from blood, bone marrow, or other tissue sources from the patient to be treated (autologous cells) or from a suitable allogenic or xenogenic donor source. In certain embodiments of the invention, the conformable compositions incorporate an enriched bone marrow fraction, prepared for example as described in US Patent Publication No. 2005/0130301 to McKay et al. published Jun. 16, 2005, publishing U.S. patent application Ser. No. 10/887,275 filed Jul. 8, 2004, which is hereby incorporated herein by reference in its entirety. Thus, implantable materials can incorporate a bone marrow fraction enriched in connective tissue growth components, that is prepared by centrifuging a biological sample (e.g. from the patient to be treated) to separate the sample into fractions including a fraction rich in connective tissue growth components. The fraction rich in connective tissue growth components can then be isolated from the separated sample, and incorporated into or onto a dry-form device of the invention, e.g. by using the fraction in or as a wetting medium applied to the device by a health care provider prior to implantation.

In still further embodiments, the present invention provides methods for treating patients that involve implanting in the patients an osteoinductive DBM device as described herein. In such uses, an osteoinductive DBM device can be implanted at a site at which tissue growth is desired, e.g. to treat a disease, defect or location of trauma, and/or in some instances to promote artificial arthrodesis. The medical devices of the invention can be used as surgical implants at, in, on, or near bone defect sites, cartilage repair sites, or other musculoskeletal sites. In certain beneficial embodiments, the device will exhibit a conformable or flexible character that enables its introduction and shaping within voids, defects or other areas in which new tissue growth is desired, and/or in certain embodiments in which the delivery of a bioactive agent is desired. Further in this regard, the device can have compression-resistant properties sufficient to resist substantial compression when impinged by adjacent soft tissues of the body at a bony implant site, for instance at a posterolateral spinal fusion implant site.

Illustrative bone repair sites that can be treated with medical devices of the invention include, for instance, those resulting from injury, defects brought about during the course of surgery, infection, malignancy or developmental malformation. The devices can be used in a wide variety of orthopedic, periodontal, neurosurgical and oral and maxillofacial surgical procedures including, but not limited to: the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc. Specific bones which can be repaired or replaced with the device include, but are not limited to: the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

In accordance with certain aspects of the invention, the osteoinductive DBM device can be used as a bone void filler, or can be incorporated in, on or around a load bearing implants such as spinal implants, hip implants (e.g. in or around implant stems and/or behind acetabular cups), knee implants (e.g. in or around stems). In inventive variants, the osteoinductive DBM devices can be incorporated in, on or around a load-bearing spinal implant device having a compressive strength of at least about 10000 N, such as a fusion cage, dowel, or other device potentially having a pocket, chamber or other cavity for containing an osteoinductive material, and used in a spinal fusion such as an interbody fusion. One illustrative such use is in conjunction with a load-bearing interbody spinal spacer to achieve interbody fusion. In these applications, the device can be placed in and/or around the spacer to facilitate the fusion.

Illustrative cartilage repair sites that can be treated with devices of the invention include, as examples, articular cartilage surfaces occurring in articular joints having at least two major bones. Examples include, but are not limited to the elbow, wrist, phalanx, knee, and ankle. Additionally, cartilage surfaces within shoulder and hip joints can be treated.

The present invention also provides medical kits or or other products that include one or more osteoinductive DBM devices of the invention. Such products can include the device(s) of the invention in a dried (e.g. having less than about 5% residual water) or wet format, received in sterile condition in medical packaging. Such products can also include one or more additional surgical instruments or implants, for example a load-bearing implant (e.g. a spinal spacer), and/or a fluid transfer device such as a syringe, and/or a therapeutic substance, for example an osteogenic substance such as a BMP. In one specific form, such a medical kit can include a dried device of the invention, a BMP in lyophilized form (e.g. rhBMP-2), and an aqueous medium for reconstitution of the BMP to prepare an aqueous formulation that can then be added to the dried device.

The invention will now be more particularly described with reference to the following specific examples. It will be understood that these examples are illustrative and not limiting of the embodiments of the invention.

EXAMPLE 1

Preparation of Osteoindutive DBM Devices 13.3 g of sodium alginate (USP grade, Spectrum Chemical) were combined with 1680 cc of water for injection (WFI) in a blender. The materials were mixed in the blender until all of the alginate was incorporated. The combined PBS/alginate material was then transferred to a mixer bowl and mixing was initiated. 18.2 g of milled, crosslinked collagen sponge were slowly added to the mixer bowl while mixing, and the resulting materials mixed to form a uniform mixture. The milled collagen was obtained by grinding a crosslinked collagen sponge material available from Collagen Matrix, Inc. (Franklin Lakes, N.J.) and known as Collagen Matrix Sponge. A retch grinder operating at 8000 rpm with a 1 mm sieve was used for this purpose, resulting in the collection of the randomized sponge particulate as a wispy mass. 100 g of osteoinductive demineralized bone matrix having a particle size of 55-850 µm were then slowly added to the bowl while mixing, which was allowed to proceed until a uniform mixture was obtained. 260 cc aliquots of the resulting slurry were measured in a graduated cylinder and transferred to 260 cc capacity stainless steel screen molds (270 mesh screen size). The dimensions of the molds were 8 inches (~20.3 cm) by 10 inches (~25.4 cm), and the slurry was pooled to a depth of about 0.5 cm. The molds were capped with a screen top and completely submerged in a vessel containing a 1% by weight solution of calcium chloride dihydrate for a period of 6 to 24 hours in order the ionically crosslink the alginate. The molds were then removed from the crosslinking solution, placed into individual lyophilization pouches, and lyophilized under conditions to substantially preserve the original volume of the charged material. The resulting lyophilized materials were flexible, solid sheet materials having a thickness of about 5 mm and exhibiting a bulk density in the range of about 0.17 g/cc to 0.21 g/cc. The sheets were cut to desired strip sizes (some 2 cm×5 cm and some 2 cm×9 cm) and packaged in trays in a double-pouch format. The packaged products were terminally sterilized with E-beam to a level of 25 kiloGrays (kGy).

Strip materials prepared as described above were evaluated for osteoinductivity in the widely-accepted athymic rat model. Implants were placed singularly in the muscle pouch of each hind limb near the femur to allow for blood supply but not adjacent to the bone. At 28 days post-operative, the rats were sacrificed via carbon dioxide inhalation. The implants were then harvested. Explants were placed in labeled histology cassettes in 10% neutral buffered formalin. Samples were decalcified, embedded in paraffin, sectioned & stained. Three sections per implant were taken at 100 micrometer intervals and stained with H&E. Semi-quantitative scoring of the samples versus controls confirmed that the implant materials were osteoinductive.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are hereby incorporated by reference in their entirety.

What is claimed is:

1. A demineralized bone matrix (DBM) device, comprising:
   a three-dimensionally stable, porous implant structure, wherein said structure is a resilient, porous sheet material;
   said three-dimensionally stable, porous implant structure comprising an admixture including particulate solids, said particulate solids including a particulate collagen material and a particulate DBM material in a weight ratio of 1:12 to about 1:2, respectively; and
   said admixture including particulate solids retained in the form of said porous implant structure by an ionically-crosslinked polysaccharide gel, wherein said polysaccharide is an alginate.

2. The DBM device of claim 1, wherein said porous implant structure is a lyophilized material.

3. The DBM device of claim 1, wherein said structure is comprised about 20% to about 80% by weight of said DBM material on a dry weight basis.

4. The DBM device of claim 1, wherein said structure is comprised about 5% to about 30% by weight of said collagen material on a dry weight basis.

5. The DBM device of claim 1, wherein said structure is comprised about 5% to about 20% by weight of said polysaccharide on a dry weight basis.

6. The DBM device of claim 1, wherein said particulate collagen material comprises particulated collagen sponge.

7. The DBM device of claim 1, wherein said gel is hydrated with an aqueous liquid medium.

8. The DBM device of claim 1, wherein said gel is ionically crosslinked with a calcium salt.

9. The DBM device of claim 8, wherein said calcium salt is calcium chloride.

10. The DBM device of claim 1, prepared by a process that comprises:
    forming an admixture including water, said polysaccharide, wherein said polysaccharide is an alginate, said particulate collagen material, and said particulate DBM material;
    contacting said admixture with a liquid medium containing an amount of a multivalent ionic agent effective to ionically crosslink said polysaccharide and obtain an ionically-crosslinked wet precursor material having said particulate collagen material and said particulate DBM material entrained therein;
    freezing said ionically-crosslinked wet precursor material to form a frozen precursor material; and
    drying said frozen precursor material.

11. The DBM device of claim 1, wherein said DBM material retained in said porous implant structure exhibits osteoinductivity.

12. The DBM device of claim 1, wherein said particulate DBM material is osteoinductive, and wherein said particulate solids are bound in said resilient, porous sheet material in the absence of covalent chemical crosslinking of particles of the particulate solids to one another.

* * * * *